(12) United States Patent
Liu et al.

(10) Patent No.: US 11,110,441 B2
(45) Date of Patent: Sep. 7, 2021

(54) CATALYST FOR PREPARING PYRIDINE BASE FROM SYNGAS, AND PREPARATION METHOD AND APPLICATION THEREOF

(71) Applicant: NANJING REDSUN BIOCHEMISTRY CO., LTD., Nanjing (CN)

(72) Inventors: Xiaopan Liu, Nanjing (CN); Chaoran Luo, Nanjing (CN); Yi Xue, Nanjing (CN); Wenkui Wang, Nanjing (CN); Xiang Du, Nanjing (CN)

(73) Assignee: NANJING REDSUN BIOCHEMISTRY CO., LTD, Nanjing (CN)

( * ) Notice: Subject to any disclaimer, the term of this patent is extended or adjusted under 35 U.S.C. 154(b) by 0 days.

(21) Appl. No.: 17/048,563

(22) PCT Filed: Aug. 3, 2018

(86) PCT No.: PCT/CN2018/098435
§ 371 (c)(1),
(2) Date: Oct. 16, 2020

(87) PCT Pub. No.: WO2019/200778
PCT Pub. Date: Oct. 24, 2019

(65) Prior Publication Data
US 2021/0162381 A1 Jun. 3, 2021

(30) Foreign Application Priority Data
Apr. 19, 2018 (CN) .......................... 201810353733.1

(51) Int. Cl.
| B01J 29/70 | (2006.01) |
| B01J 29/40 | (2006.01) |
| B01J 29/65 | (2006.01) |
| C07D 213/16 | (2006.01) |
| B01J 29/48 | (2006.01) |
| B01J 29/69 | (2006.01) |
| B01J 29/78 | (2006.01) |
| C07D 213/10 | (2006.01) |
| B01J 29/68 | (2006.01) |
| B01J 29/76 | (2006.01) |
| B01J 29/46 | (2006.01) |

(52) U.S. Cl.
CPC ............... B01J 29/48 (2013.01); B01J 29/40 (2013.01); B01J 29/405 (2013.01); B01J 29/46 (2013.01); B01J 29/65 (2013.01); B01J 29/655 (2013.01); B01J 29/68 (2013.01); B01J 29/69 (2013.01); B01J 29/7038 (2013.01); B01J 29/7088 (2013.01); B01J 29/7676 (2013.01); B01J 29/7876 (2013.01); C07D 213/10 (2013.01); B01J 2229/18 (2013.01); B01J 2229/186 (2013.01); C07D 213/16 (2013.01)

(58) Field of Classification Search
CPC ............ B01J 29/44–48; B01J 29/67–69; B01J 29/7476; B01J 29/7676; B01J 29/7876; B01J 2229/186; C07D 213/16
See application file for complete search history.

(56) References Cited

U.S. PATENT DOCUMENTS

| 7,045,671 B2 * | 5/2006 | Schmidt ................. B01J 29/405 502/60 |
| 8,575,054 B2 * | 11/2013 | Ikoma ................ B01D 53/8621 502/60 |
| 9,827,560 B2 * | 11/2017 | Petushkov ............... B01J 29/68 |
| 2004/0077493 A1 | 4/2004 | Antonelli |

(Continued)

FOREIGN PATENT DOCUMENTS

| CN | 1225852 A | 8/1999 |
| CN | 102294260 A | 12/2011 |

(Continued)

OTHER PUBLICATIONS

Wang et al., "Organonitrogen Chemicals from Oxygen-Containing Feedstock over Heterogeneous Catalysts", ACS Catal. 2020, 10, 1, 311-335 (Year: 2020).*
Kandepi et al., "Synthesis of N-heterocyclic compounds over zeolite molecular sieve catalysts: an approach towards green chemistry†", Catal. Sci. Technol., 2012, 2, 471-487 (Year: 2012).*
Lee et al., "Rhodium supported on thermally enhanced zeolite as catalysts for fuel reformation of jet fuels", Catalysis Today vol. 136, Issues 3-4, Jul. 31, 2008, pp. 258-265 (Year: 2008).*
Yang et al, "The influence of alkali-treated zeolite on the oxide-zeolite syngas conversion process†", Catal. Sci. Technol., 2018, 8, 4338-4348 (Year: 2018).*
Portugal et al., CO2 reforming of CH4 over Rh-containing catalysts, Journal of Molecular Catalysis A: Chemical 184 (2002) 311-322 (Year: 2002).*

(Continued)

Primary Examiner — David M Brunsman
(74) Attorney, Agent, or Firm — Gary J. Gershik

(57) ABSTRACT

The present invention discloses a catalyst for preparing pyridine base from syngas. The catalyst includes a carrier, an active component, a first auxiliary and a second auxiliary. The carrier is molecular sieves. The active component is Rh. The first auxiliary is one or more of Mn, Fe, Na and La. The second auxiliary is one or more of Zn, Co, Cr, Bi and Cu. The active component Rh is 0.5-3% of a mass of the carrier. The first auxiliary is 0.05-5% of the mass of the carrier. The second auxiliary is 0.5-15% of the mass of the carrier. The present invention further discloses application of the catalyst to preparation of pyridine base by catalyzing syngas, where the syngas and an ammonia donor are used as reaction raw materials for reaction to generate pyridine base products. The catalyst of the present invention can couple a cyclization reaction of generating acetaldehyde through hydrogenation of carbon monoxide with a condensation reaction of aldehyde and ammonia to convert the syngas into the pyridine base through one-step catalysis, with a carbon monoxide conversion rate of 8-20% and a pyridine base selectivity of 10-18%.

10 Claims, No Drawings

(56) References Cited

U.S. PATENT DOCUMENTS

2019/0284115 A1* 9/2019 Ramakrishna ....... B01J 35/1019

FOREIGN PATENT DOCUMENTS

| CN | 103301849 A | 9/2013 |
|----|----|----|
| WO | WO 2019/200778 A1 | 10/2019 |

OTHER PUBLICATIONS

International Search Report dated Jan. 29, 2019 in connection with PCT International Application No. PCT/CN2018/098435.
Written Opinion (form PCT/ISA/237) dated Jan. 29, 2019 in connection with PCT International Application No. PCT/CN2018/098435.

* cited by examiner

CATALYST FOR PREPARING PYRIDINE BASE FROM SYNGAS, AND PREPARATION METHOD AND APPLICATION THEREOF

CROSS-REFERENCE TO RELATED APPLICATIONS

This application is a § 371 national stage of PCT International Application No. PCT/CN2018/098435, filed Aug. 3, 2018, claiming priority of Chinese Patent Application No. CN 201810353733.1, filed Apr. 19, 2018, the contents of each of which are hereby incorporated by reference herein.

BACKGROUND

Technical Field

The present invention belongs to the technical field of catalysts, and particularly relates to a catalyst for preparing pyridine base from syngas, and a preparation method and application thereof.

Related Art

Pyridine base is commonly known as a "chip" of heterocyclic pesticides, medicines and veterinary drug and intermediates thereof, is a nitrogenous heterocyclic compound of the heterocyclic pesticides, medicines and veterinary drugs and intermediates thereof under key encouragement of the state, and is also an important raw material of daily chemical, food and feed additives.

At present, catalyzing cyclization and condensation of aldehyde and ammonia by a ZSM-5 molecular sieve to generate pyridine compounds is the most common method for producing pyridine base industrially. Acetaldehyde as an important raw material in a reaction is usually produced by an ethylene oxidation method, an ethanol oxidation method or an acetylene synthesis method industrially. Although these processes are mature, they have the defects of high energy consumption and high dependence on petroleum resources and the like. Syngas is a mixture with carbon monoxide and hydrogen as main components and has the characteristics of wide sources, low price and the like. Exploring a novel process for preparing pyridine base from syngas has great significance in the pyridine industry and the C1 chemical field.

So far, there have been no reports on catalysts and related processes for preparing pyridine base from syngas, but there have been many reports on preparation of C2 oxygenated chemicals from syngas. The Chinese patent CN1354043A disclosed a rhodium-based catalyst for preparing C2 oxygenated chemicals from syngas, the catalyst adopted MCM-41 or MCM-22 with a high silica-alumina ratio as a carrier, and the highest selectivity of the C2 oxygenated chemicals is 55.4%. The Chinese patent CN1175479A disclosed a catalyst for preparing ethanol, acetaldehyde and other C2 oxygenated chemicals through hydrogenation of carbon monoxide, the catalyst belongs to a Rh—V-M/$SiO_2$ catalyst system, M is one or more elements of Ru, Fe, Ir, Mo, Mn, K, Li, Zr or Cu, the catalyst can efficiently convert carbon monoxide and hydrogen into ethanol and acetaldehyde products, and an ethanol and acetaldehyde selectivity of 1% Rh-1.5% V-0.5% Fe-0.1% Ir-0.1% K/$SiO_2$ catalyst is 86%.

SUMMARY

An objective of the present invention is to provide a catalyst for preparing pyridine base from syngas, and the catalyst can catalyze carbon monoxide, hydrogen and ammonia in one step to generate pyridine, 2-methylpyridine, 3-methylpyridine, 4-methylpyridine and other pyridine base products.

The objective of the present invention is achieved through the following technical scheme.

The catalyst for preparing pyridine base from syngas includes a carrier, an active component, a first auxiliary and a second auxiliary. The carrier is a molecular sieve. The active component is Rh. The first auxiliary is one or more of Mn, Fe, Na and La. The second auxiliary is one or more of Zn, Co, Cr, Bi and Cu.

The active component Rh is 0.5-3% of a mass of the carrier, preferably 1-3%. The first auxiliary is 0.05-5% of the mass of the carrier, preferably 1.5-5%. The second auxiliary is 0.5-15% of the mass of the carrier, preferably 5-11%.

The molecular sieve is one or more of an HZSM-5 molecular sieve, an HZSM-11 molecular sieve, an HZSM-35 molecular sieve and an MCM-22 molecular sieve, preferably one or more of an HZSM-5 molecular sieve, an HZSM-11 molecular sieve, an HZSM-35 molecular sieve and an MCM-22 molecular sieve with a silica-alumina ratio of 50-150, and further preferably one or more of an HZSM-5 molecular sieve and an HZSM-11 molecular sieve with a silica-alumina ratio of 50-150.

Another objective of the present invention is to provide a preparation method of the catalyst for preparing pyridine base from syngas. The preparation method includes:

step (1): dissolving a rhodium salt and metal salts corresponding to a first auxiliary and a second auxiliary in a solvent to obtain a metal salt solution, and evenly mixing a carrier with the metal salt solution and impregnating at room temperature for 0.5-48 h; and step (2): vacuum drying the mixture obtained in step (1) at 80-120° C. for 0.5-4 h, and calcining at 300-550° C. for 1-5 h to obtain the catalyst for preparing the pyridine base from the syngas; or step (1): dissolving a rhodium salt in a solvent to obtain a rhodium salt solution, and evenly mixing a carrier with the rhodium salt solution and impregnating at room temperature for 0.5-48 h;

step (2): vacuum drying the mixture obtained in step (1) at 80-120° C. for 0.5-4 h and calcining at 300-550° C. for 1-5 h to prepare a precursor loaded with an active component Rh;

step (3): dissolving a metal salt corresponding to an auxiliary in a solvent to obtain a metal salt solution, and evenly mixing the precursor prepared in step (2) with the metal salt solution and impregnating at room temperature for 0.5-48 h; and step (4): vacuum drying the mixture obtained in step (3) at 80-120° C. for 0.5-4 h and calcining at 300-550° C. for 1-5 h to obtain the catalyst for preparing the pyridine base from the syngas; or step (1): dissolving a metal salt corresponding to an auxiliary in a solvent to obtain a metal salt solution, and evenly mixing a molecular sieve with the metal salt solution and impregnating at room temperature for 0.5-48 h;

step (2): vacuum drying the mixture obtained in step (1) at 80-120° C. for 0.5-4 h and calcining at 300-550° C. for 1-5 h to prepare a precursor loaded with the auxiliary;

step (3): dissolving a rhodium salt in a solvent to obtain a rhodium salt solution, and evenly mixing the precursor prepared in step (2) with the rhodium salt solution and impregnating at room temperature for 0.5-48 h; and step (4): vacuum drying the mixture obtained in step (3) at 80-120° C. for 0.5-4 h and calcining at 300-550° C. for 1-5 h to obtain the catalyst for preparing the pyridine base from the syngas.

The rhodium salt is rhodium chloride, the metal salt corresponding to the first auxiliary Mn, Fe, Na and La is nitrate, and the metal salt corresponding to the second auxiliary Zn, Co, Cr, Bi and Cu is nitrate.

The solvent is one or more of deionized water, methanol, ethanol and isopropanol.

Application of the catalyst of the present invention to preparation of pyridine base by catalyzing syngas is provided.

A method for preparing pyridine base from syngas by catalysis of the catalyst of the present invention includes the following steps: with the syngas and an ammonia donor as reaction raw materials, a molar ratio of $H_2$ to CO in the syngas being (1-5):1 and a molar ratio of the ammonia donor by $NH_3$ to CO being 1:(1-100), introducing the reaction raw materials into a fixed bed reactor filled with the catalyst of the present invention at a space velocity of 5000-15000 $h^{-1}$ for reaction at a reaction temperature of 250-400° C. under a reaction pressure of 1-5 MPa to obtain a pyridine base product, and absorbing the pyridine base product with deionized water.

The ammonia donor is selected from one or more of ammonia gas, liquid ammonia and ammonia water.

The pyridine base is one or more of pyridine, 2-methylpyridine, 3-methylpyridine and 4-methylpyridine.

The active component, the first auxiliary and the second auxiliary in the catalyst of the present invention exist in a form of metal elements or oxides. The catalyst is subjected to reduction treatment with hydrogen before use, and the reduction treatment is carried out by filling a constant-temperature section of the fixed bed reactor with the catalyst at a hydrogen space velocity of 500-1200 $h^{-1}$ and a reduction temperature of 250-450° C. for a reaction time of 1-5 h.

The present invention has the following beneficial effects:

The Rh and the first auxiliary in the catalyst of the present invention jointly catalyze efficient conversion of the carbon monoxide and the hydrogen into acetaldehyde and ethanol and selectively oxidize the generated ethanol into acetaldehyde in the presence of the second auxiliary, and then the acetaldehyde and ammonia are catalyzed by acid sites of the molecular sieve to generate the pyridine base product. The catalyst of the present invention can couple a cyclization reaction of generating acetaldehyde through hydrogenation of carbon monoxide with a condensation reaction of aldehyde and ammonia to convert the syngas into the pyridine base through one-step catalysis, with a carbon monoxide conversion rate of 8-20% and a pyridine base selectivity of 10-18% which is significantly higher than that of catalysts only including the first auxiliary or the second auxiliary.

In addition, the present invention provides a new concept for production of the pyridine base and deep utilization of the syngas and has broad market prospects.

DETAILED DESCRIPTION

The technical scheme of the present invention is specifically described with reference to examples below.

Example 1

Step (1). 0.1283 g of $RhCl_3 \cdot 3H_2O$, 0.3914 g of $Mn(NO_3)_2 \cdot 6H_2O$, 0.0361 g of $Fe(NO_3)_3 \cdot 9H_2O$, 0.0311 g of $La(NO_3)_3 \cdot 6H_2O$ and 1.1423 g of $Zn(NO_3)_2 \cdot 6H_2O$ were dissolved in 5 g of absolute ethyl alcohol and evenly stirred to obtain a uniform metal salt solution, and 5 g of HZSM-5 molecular sieve (silica-alumina ratio: 120) was evenly mixed with the metal salt solution and impregnated at room temperature for 4 h.

Step (2). The mixture obtained in step (1) was vacuum dried at 80° C. for 2 h and calcined at 350° C. for 2 h. The product obtained was designated as 1.0Rh-1.5Mn-0.1Fe-0.2La-5.0Zn/HZSM-5 (1.0Rh represents that a mass of Rh atoms is 1% of a mass of the carrier, similarly hereinafter).

Example 2

Step (1). 0.1919 g of $RhCl_3 \cdot 3H_2O$, 0.3914 g of $Mn(NO_3)_2 \cdot 6H_2O$, 0.1083 g of $Fe(NO_3)_3 \cdot 9H_2O$, 0.4932 g of $Co(NO_3)_2 \cdot 6H_2O$ and 3.8462 g of $Cr(NO_3)_3 \cdot 9H_2O$ were dissolved in 5 g of ethanol and evenly stirred to obtain a uniform metal salt solution, and 5 g of HZSM-11 molecular sieve (silica-alumina ratio: 120) was evenly mixed with the metal salt solution and impregnated at room temperature for 10 h.

Step (2). The mixture obtained in step (1) was vacuum dried at 100° C. for 1 h and calcined at 400° C. for 1.5 h. The product obtained was designated as 1.5Rh-1.5Mn-0.3Fe-2.0Co-10Cr/HZSM-11.

Example 3

Step (1). 0.1577 g of $Rh(NO_3)_3 \cdot 2H_2O$ was dissolved in 5 g of deionized water and evenly stirred to obtain a uniform rhodium chloride solution, and 5 g of HZSM-35 molecular sieve (silica-alumina ratio: 120) was evenly mixed with the rhodium chloride solution.

Step (2). The mixture obtained in step (1) was impregnated at room temperature for 2 h, vacuum dried at 100° C. for 0.5 h, and calcined at 500° C. for 4 h to obtain a precursor 1.0Rh/HZSM-35.

Step (3). 0.1305 g of $Mn(NO_3)_2 \cdot 6H_2O$, 0.9018 g of $Fe(NO_3)_3 \cdot 9H_2O$, 0.1142 g of $Zn(NO_3)_2 \cdot 6H_2O$, 1.9231 g of $Cr(NO_3)_3 \cdot 9H_2O$ and 0.3766 g of $Cu(NO_3)_2 \cdot 3H_2O$ were dissolved in 5 g of deionized water and evenly stirred to obtain a uniform metal salt solution, and the precursor 1.0Rh/HZSM-35 prepared in step (2) was evenly mixed with the metal salt solution and impregnated at room temperature for 2 h.

Step (4). The mixture obtained in step (3) was vacuum dried at 100° C. for 0.5 h and calcined at 500° C. for 4 h. The product obtained was designated as 1.0Rh-0.05Mn-2.5Fe-0.5Zn-2.0Cu-5.0Cr/HZSM-35.

Example 4

Step (1). 0.1921 g of $RhCl_3 \cdot 3H_2O$ was dissolved in 5 g of ethanol and evenly stirred to obtain a uniform rhodium chloride solution, and 5 g of an HZSM-5 molecular sieve (silica-alumina ratio: 120) was evenly mixed with the rhodium chloride solution.

Step (2). The mixture obtained in step (1) was impregnated at room temperature for 24 h, vacuum dried at 110° C. for 3 h, and calcined at 550° C. for 3 h to obtain a precursor 1.5Rh/HZSM-5.

Step (3). 0.6523 g of $Mn(NO_3)_2 \cdot 6H_2O$, 0.3115 g of $La(NO_3)_3 \cdot 6H_2O$ and 2.4661 g of $Co(NO_3)_2 \cdot 6H_2O$ were dissolved in 5 g of ethanol and evenly stirred to obtain a uniform metal salt solution, and the precursor 1.5Rh/HZSM-5 prepared in step (2) was evenly mixed with the metal salt solution and impregnated at room temperature for 24 h.

Step (4). The mixture obtained in step (3) was vacuum dried at 110° C. for 3 h and calcined at 550° C. for 3 h. The product obtained was designated as 1.5Rh-2.5Mn-2.0La-10.0Co/HZSM-5.

Example 5

Step (1). 0.1577 g of $Rh(NO_3)_3 \cdot 2H_2O$ was dissolved in 5 g of deionized water and evenly stirred to obtain a uniform rhodium chloride solution, and 5 g of HZSM-11 molecular sieve (silica-alumina ratio: 120) was evenly mixed with the rhodium chloride solution and impregnated at room temperature for 48 h.

Step (2). The mixture obtained in step (1) was vacuum dried at 120° C. for 3 h and calcined at 300° C. for 3 h to obtain a precursor 1.0Rh/HZSM-11.

Step (3). 0.3914 g of $Mn(NO_3)_2 \cdot 6H_2O$, 0.0361 g of $Fe(NO_3)_3 \cdot 9H_2O$, 0.0580 g of $Bi(NO_3)_3 \cdot 5H_2O$ and 1.9009 g of $Cu(NO_3)_2 \cdot 3H_2O$ were dissolved in 5 g of deionized water and evenly stirred to obtain a uniform metal salt solution, and the precursor 1.0Rh/HZSM-11 prepared in step (2) was evenly mixed with the metal salt solution and impregnated at room temperature for 48 h.

Step (4). The mixture obtained in step (3) was vacuum dried at 120° C. for 3 h and calcined at 300° C. for 3 h. The product obtained was designated as 1.0Rh-1.5Mn-0.1Fe-0.5Bi-10.0Cu/HZSM-11.

Example 6

Step (1). 0.3914 g of $Mn(NO_3)_2 \cdot 6H_2O$, 0.0184 g of $NaNO_3$, 2.2846 g of $Zn(NO_3)_2 \cdot 6H_2O$ and 0.0941 g of $Cu(NO_3)_2 \cdot 3H_2O$ was dissolved in 5 g of deionized water and evenly stirred to obtain a uniform metal salt solution, and 5 g of HZSM-11 molecular sieve (silica-alumina ratio: 120) was evenly mixed with the metal salt solution and impregnated at room temperature for 8 h.

Step (2). The mixture obtained in step (1) was vacuum dried at 100° C. for 4 h and calcined at 350° C. for 2.5 h to obtain a precursor 1.5Mn-0.1Na-10.0Zn-0.5Cu/HZSM-11.

Step (3). 0.3837 g of $RhCl_3 \cdot 3H_2O$ was dissolved in 5 g of deionized water and evenly stirred to obtain a uniform rhodium chloride solution, and the precursor 1.5Mn-0.1Na-10.0Zn-0.5Cu/HZSM-11 prepared in step (2) was evenly mixed with the rhodium chloride solution and impregnated at room temperature for 8 h.

Step (4). The mixture obtained in step (3) was vacuum dried at 100° C. for 4 h and calcined at 350° C. for 2.5 h. The product obtained was designated as 3.0Rh-1.5Mn-0.1Na-10.0Zn-0.5Cu/HZSM-11.

Example 7

Step (1). 0.3914 g of $Mn(NO_3)_2 \cdot 6H_2O$, 0.1233 g of $Co(NO_3)_2 \cdot 6H_2O$, 0.1923 g of $Cr(NO_3)_3 \cdot 9H_2O$ and 0.5801 g of $Bi(NO_3)_3 \cdot 5H_2O$ were dissolved in 5 g of deionized water and evenly stirred to obtain a uniform metal salt solution, and 5 g of MCM-22 molecular sieve (silica-alumina ratio: 50) was evenly mixed with the metal salt solution and impregnated at room temperature for 15 h.

Step (2). The mixture obtained in step (1) was vacuum dried at 100° C. for 4 h and calcined at 400° C. for 2 h to obtain a precursor 1.5Mn-0.5Co-5.0Bi-0.5Cr/MCM-22.

Step (3). 0.0642 g of $RhCl_3 \cdot 3H_2O$ was dissolved in 5 g of ethanol and evenly stirred to obtain a uniform rhodium chloride solution, and the precursor 1.5Mn-0.5Co-5.0Bi-0.5Cr/MCM-22 prepared in step (2) was evenly mixed with the rhodium chloride solution and impregnated at room temperature for 15 h.

Step (4). The mixture obtained in step (3) was vacuum dried at 100° C. for 4 h and calcined at 400° C. for 2 h. The product obtained was designated as 0.5Rh-1.5Mn-0.5Co-5.0Bi-0.5Cr/MCM-22.

Example 8

Step (1). 0.3914 g of $Mn(NO_3)_2 \cdot 6H_2O$, 0.0722 g of $Fe(NO_3)_3 \cdot 9H_2O$, 0.0184 g of $NaNO_3$ and 1.1602 g of $Bi(NO_3)_3 \cdot 5H_2O$ were dissolved in 5 g of deionized water and evenly stirred to obtain a uniform metal salt solution, and 5 g of HZSM-5 molecular sieve (silica-alumina ratio: 120) was evenly mixed with the metal salt solution and impregnated at room temperature for 10 h.

Step (2). The mixture obtained in step (1) was vacuum dried at 120° C. for 3 h and calcined at 450° C. for 5 h to obtain a precursor 1.5Mn-0.2Fe-0.1Na-10.0Bi/HZSM-5.

Step (3). 0.2547 g of $RhCl_3 \cdot 3H_2O$ was dissolved in 5 g of deionized water and evenly stirred to obtain a uniform rhodium chloride solution, and the precursor 1.5Mn-0.2Fe-0.1Na-10.0Bi/HZSM-5 prepared in step (2) was evenly mixed with the rhodium chloride solution and impregnated at room temperature for 10 h.

Step (4). The mixture obtained in step (3) was vacuum dried at 120° C. for 3 h and calcined at 450° C. for 5 h. The product obtained was designated as 2.0Rh-1.5Mn-0.2Fe-0.1Na-10.0Bi/HZSM-5.

Comparative Example 1

Step (1). 0.3914 g of $Mn(NO_3)_2 \cdot 6H_2O$, 0.0722 g of $Fe(NO_3)_3 \cdot 9H_2O$ and 0.0184 g of $NaNO_3$ were dissolved in 5 g of deionized water and evenly stirred to obtain a uniform metal salt solution, and 5 g of HZSM-5 molecular sieve (silica-alumina ratio: 120) was evenly mixed with the metal salt solution and impregnated at room temperature for 10 h.

Step (2). The mixture obtained in step (1) was vacuum dried at 120° C. for 3 h and calcined at 450° C. for 5 h to obtain a precursor 1.5Mn-0.2Fe-0.1Na/HZSM-5.

Step (3). 0.2547 g of $RhCl_3 \cdot 3H_2O$ was dissolved in 5 g of deionized water and evenly stirred to obtain a uniform rhodium chloride solution, and the precursor 1.5Mn-0.2Fe-0.1Na/HZSM-5 prepared in step (2) was evenly mixed with the rhodium chloride solution and impregnated at room temperature for 10 h.

Step (4). The mixture obtained in step (3) was vacuum dried at 120° C. for 3 h and calcined at 450° C. for 5 h. The product obtained was designated as 2.0Rh-1.5Mn-0.2Fe-0.1Na/HZSM-5.

Comparative Example 2

Step (1). 1.1602 g of $Bi(NO_3)_3 \cdot 5H_2O$ was dissolved in 5 g of deionized water and evenly stirred to obtain a uniform metal salt solution, and 5 g of HZSM-5 molecular sieve (silica-alumina ratio: 120) was evenly mixed with the metal salt solution and impregnated at room temperature for 10 h.

Step (2). The mixture obtained in step (1) was vacuum dried at 120° C. for 3 h and calcined at 450° C. for 5 h to obtain a precursor 10.0Bi/HZSM-5.

Step (3). 0.2547 g of $RhCl_3 \cdot 3H_2O$ was dissolved in 5 g of deionized water and evenly stirred to obtain a uniform rhodium chloride solution, and the precursor 10.0Bi/

HZSM-5 prepared in step (2) was evenly mixed with the rhodium chloride solution and impregnated at room temperature for 10 h.

Step (4). The mixture obtained in step (3) was vacuum dried at 120° C. for 3 h and calcined at 450° C. for 5 h. The product obtained was designated as 2.0Rh-10.0Bi/HZSM-5.

Comparative Example 3

Step (1). 0.3914 g of $Mn(NO_3)_2 \cdot 6H_2O$, 0.0722 g of $Fe(NO_3)_3 \cdot 9H_2O$, 0.0184 g of $NaNO_3$ and 1.1602 g of $Bi(NO_3)_3 \cdot 5H_2O$ were dissolved in 5 g of deionized water and evenly stirred to obtain a uniform metal salt solution, and 5 g of MCM-41 molecular sieve (all-silicon molecular sieve) was evenly mixed with the metal salt solution and impregnated at room temperature for 10 h.

Step (2). The mixture obtained in step (1) was vacuum dried at 120° C. for 3 h and calcined at 450° C. for 5 h to obtain a precursor 1.5Mn-0.2Fe-0.1Na-10.0Bi/MCM-41.

Step (3). 0.2547 g of $RhCl_3 \cdot 3H_2O$ was dissolved in 5 g of deionized water and evenly stirred to obtain a uniform rhodium chloride solution, and the precursor 1.5Mn-0.2Fe-0.1Na-10.0Bi/MCM-41 prepared in step (2) was evenly mixed with the rhodium chloride solution and impregnated at room temperature for 10 h.

Step (4). The mixture obtained in step (3) was vacuum dried at 120° C. for 3 h and calcined at 450° C. for 5 h. The product obtained was designated as 2.0Rh-1.5Mn-0.2Fe-0.1Na-10.0Bi/MCM-41.

Comparative Example 4

Step (1). 0.3914 g of $Mn(NO_3)_2 \cdot 6H_2O$, 0.0722 g of $Fe(NO_3)_3 \cdot 9H_2O$, 0.0184 g of $NaNO_3$ and 1.1602 g of $Bi(NO_3)_3 \cdot 5H_2O$ were dissolved in 5 g of deionized water and evenly stirred to obtain a uniform metal salt solution, and 5 g of $SiO_2$ was evenly mixed with the metal salt solution and impregnated at room temperature for 10 h.

Step (2). The mixture obtained in step (1) was vacuum dried at 120° C. for 3 h and calcined at 450° C. for 5 h to obtain a precursor 1.5Mn-0.2Fe-0.1Na-10.0Bi/$SiO_2$.

Step (3). 0.2547 g of $RhCl_3 \cdot 3H_2O$ was dissolved in 5 g of deionized water and evenly stirred to obtain a uniform rhodium chloride solution, and the precursor 1.5Mn-0.2Fe-0.1Na-10.0Bi/$SiO_2$ prepared in step (2) was evenly mixed with the rhodium chloride solution and impregnated at room temperature for 10 h.

Step (4). The mixture obtained in step (3) was vacuum dried at 120° C. for 3 h and calcined at 450° C. for 5 h. The product obtained was designated as 2.0Rh-1.5Mn-0.2Fe-0.1Na-10.0Bi/$SiO_2$.

Performance Examination of Catalyst

Catalytic performance of the catalyst prepared in Examples 1-8 and Comparative examples 1-4 is evaluated by using a fixed bed reactor.

Specific method: 1.5 g of tablets was taken and smashed into a 20-40-mesh catalyst, and charged into a constant-temperature section of the fixed bed reactor with the catalyst, where a reaction tube with an inner diameter of 19 mm and a tube length of 700 mm is adopted as the reactor. Before the reaction started, the catalyst was subjected to reduction through pure hydrogen at a hydrogen space velocity of 800 $h^{-1}$ and a reduction temperature of 350° C. for a reduction time of 3 h. After the reduction ended, the temperature was lowered to 320° C., syngas with a ratio of $H_2/CO$ being 2:1 was introduced, a pressure of a system was raised to 3.0 MPa, and liquid ammonia was introduced according to a molar ratio of $CO:NH_3$ being 10:1 at a reaction raw material total space velocity of 8000 $h^{-1}$. A mixed product including pyridine base was absorbed with deionized water, and pyridine base product in a water phase and carbon monoxide in fixed gas were analyzed and reaction results thereof were compared 3 h after the reaction.

The reaction for preparing the pyridine base from the syngas is a cascade reaction of hydrogenation of carbon monoxide by catalysis of active sites of Rh and condensation of aldehyde and ammonia under catalysis of acid sites, and both the active sites of Rh and the acid sites of the carrier are indispensable. It can be seen from Table 1 that by selecting the HZSM-5 molecular sieve, the HZSM-11 molecular sieve and the HZSM-35 molecular sieve as the carrier of the catalyst, since the carrier has a proper pore structure and the acid sites, Rh catalyzes carbon monoxide and hydrogen to generate acetaldehyde under a synergistic action of the first auxiliary and the second auxiliary, and then an aldehyde and ammonia condensation reaction further occurs to generate the pyridine base product. Though the MCM-22 molecular sieve has a proper acid strength, due to its large twelve-membered ring supercage structure, acetaldehyde and ammonia are prone to having deep dehydrogenation and other side reactions in the supercage to generate large-molecular carbon deposits to block pores, and a CO conversion rate is lower than that of the HZSM molecular sieve, however an ideal catalytic effect can still be acquired. MCM-41 and $SiO_2$ as the carrier can hardly catalyze acetaldehyde and ammonia to further have an aldehyde and ammonia condensation reaction due to its weak acidity.

TABLE 1

Performance examination of catalyst

| Catalyst | CO conversion rate (%) | Pyridine base selectivity (%) | | | | |
|---|---|---|---|---|---|---|
| | | Pyridine | 2-methylpyridine | 3-methylpyridine | 4-methylpyridine | Total selectivity |
| 1.0Rh—1.5Mn—0.1Fe—0.2La—5.0Zn/HZSM-5 | 12.5 | 3.6 | 5.5 | 0.0 | 7.2 | 16.3 |
| 1.5Rh—1.5Mn—0.3Fe—2.0Co—10.0Cr/HZSM-11 | 15.7 | 2.1 | 4.3 | 0.1 | 5.6 | 12.1 |
| 1.0Rh—0.05Mn—2.5Fe—0.5Zn—2.0Cu—5.0Cr/HZSM-35 | 10.9 | 2.3 | 3.1 | 0.0 | 5.1 | 10.5 |
| 1.5Rh—2.5Mn—2.0La—10.0Co/HZSM-5 | 16.4 | 3.5 | 6.2 | 0.2 | 7.2 | 17.1 |
| 1.0Rh—1.5Mn—0.1Fe—0.5Bi—10.0Cu/HZSM-11 | 11.5 | 3.2 | 5.0 | 0.1 | 6.6 | 14.9 |
| 3.0Rh—1.5Mn—0.1Na—10.0Zn—0.5Cu/HZSM-11 | 20.0 | 2.7 | 7.6 | 0.3 | 6.1 | 16.7 |
| 0.5Rh—1.5Mn—0.5Co—5.0Bi—0.5Cr/MCM-22 | 8.1 | 1.5 | 4.9 | 0.0 | 4.0 | 10.4 |

TABLE 1-continued

Performance examination of catalyst

| Catalyst | CO conversion rate (%) | Pyridine base selectivity (%) | | | | |
|---|---|---|---|---|---|---|
| | | Pyridine | 2-methylpyridine | 3-methylpyridine | 4-methylpyridine | Total selectivity |
| 2.0Rh—1.5Mn—0.2Fe—0.1Na—10.0Bi/HZSM-5 | 17.2 | 4.3 | 6.8 | 0.2 | 6.3 | 17.6 |
| 2.0Rh—1.5Mn—0.2Fe—0.1Na/HZSM-5 | 16.9 | 1.8 | 3.7 | 0.0 | 2.2 | 7.7 |
| 2.0Rh—10.0Bi/HZSM-5 | 5.1 | 0.5 | 0.7 | 0.0 | 0.6 | 1.8 |
| 2.0Rh—1.5Mn—0.2Fe—0.1Na—10.0Bi/MCM-41 | 10.2 | 0.6 | 1.0 | 0.1 | 0.8 | 2.5 |
| 2.0Rh—1.5Mn—0.2Fe—0.1Na—10.0Bi/SiO$_2$ | 13.6 | 0 | 0.1 | 0 | 0.2 | 0.3 |

What is claimed is:

1. A catalyst for preparing a pyridine base from a syngas, comprising a carrier, an active component, a first auxiliary agent and a second auxiliary agent, wherein the carrier is a molecular sieve, the active component is Rh, the first auxiliary agent is one or more of Mn, Fe, Na and La, and the second auxiliary agent is one or more of Zn, Co, Cr, Bi and Cu,
wherein the active component Rh is 0.5-3% of the mass of the carrier, the first auxiliary agent is 0.05-5% of the mass of the carrier, and the second auxiliary agent is 0.5-15% of the mass of the carrier, and
wherein the molecular sieve is one or more of an HZSM-5 molecular sieve, an HZSM-11 molecular sieve, an HZSM-35 molecular sieve and an MCM-22 molecular sieve.

2. The catalyst according to claim 1, wherein the active component Rh is 1-3% of the mass of the carrier, the first auxiliary agent is 1.5-5% of the mass of the carrier, and the second auxiliary agent is 5-11% of the mass of the carrier.

3. The catalyst of claim 1, wherein the molecular sieve is one or more of an HZSM-5 molecular sieve, an HZSM-11 molecular sieve, an HZSM-35 molecular sieve and an MCM-22 molecular sieve with a silica-alumina ratio of 50-150.

4. The catalyst of claim 3, wherein the molecular sieve is one or more of an HZSM-5 molecular sieve and an HZSM-11 molecular sieve with a silica-alumina ratio of 50-150.

5. A preparation method of the catalyst for preparing a pyridine base from a syngas according to claim 1, comprising:
step (1) dissolving a rhodium salt and metal salts corresponding to a first auxiliary agent and a second auxiliary agent in a solvent to obtain a metal salt solution, and evenly mixing a carrier with the metal salt solution and impregnating at room temperature for 0.5-48 h, and
step (2) vacuum drying the mixture obtained in step (1) at 80-120° C. for 0.5-4 h, and calcining at 300-550° C. for 1-5 h to obtain the catalyst for preparing the pyridine base from the syngas; or
step (1) dissolving a rhodium salt in a solvent to obtain a rhodium salt solution, and evenly mixing a carrier with the rhodium salt solution and impregnating at room temperature for 0.5-48 h,
step (2) vacuum drying the mixture obtained in step (1) at 80-120° C. for 0.5-4 h, and calcining at 300-550° C. for 1-5 h to prepare a precursor loaded with an active component Rh,
step (3) dissolving a metal salt corresponding to an auxiliary agent in a solvent to obtain a metal salt solution, and evenly mixing the precursor prepared in step (2) with the metal salt solution and impregnating at room temperature for 0.5-48 h, and
step (4) vacuum drying the mixture obtained in step (3) at 80-120° C. for 0.5-4 h, and calcining at 300-550° C. for 1-5 h to obtain the catalyst for preparing the pyridine base from the syngas; or
step (1) dissolving a metal salt corresponding to an auxiliary agent in a solvent to obtain a metal salt solution, and evenly mixing a molecular sieve with the metal salt solution and impregnating at room temperature for 0.5-48 h,
step (2) vacuum drying the mixture obtained in step (1) at 80-120° C. for 0.5-4 h, and calcining at 300-550° C. for 1-5 h to prepare a precursor loaded with the auxiliary agent,
step (3) dissolving a rhodium salt in a solvent to obtain a rhodium salt solution, and evenly mixing the precursor prepared in step (2) with the rhodium salt solution and impregnating at room temperature for 0.5-48 h, and
step (4) vacuum drying the mixture obtained in step (3) at 80-120° C. for 0.5-4 h, and calcining at 300-550° C. for 1-5 h to obtain the catalyst for preparing the pyridine base from the syngas.

6. The preparation method of the catalyst according to claim 5, wherein the rhodium salt is rhodium chloride, the metal salt corresponding to the first auxiliary agent Mn, Fe, Na and La is nitrate, and the metal salt corresponding to the second auxiliary agent Zn, Co, Cr, Bi and Cu is nitrate, and the solvent is one or more of deionized water, methanol, ethanol, and isopropanol.

7. A method for preparing a pyridine base from a syngas through catalysis using the catalyst according to claim 1, comprising: taking the syngas and an ammonia donor as reaction raw materials, a molar ratio of $H_2$ to CO in the syngas being (1-5):1 and a molar ratio of the ammonia donor by $NH_3$ to CO being 1:(1-100); introducing the reaction raw materials into a fixed bed reactor filled with the catalyst according to claim 1 at a space velocity of 5000-15000 h$^{-1}$ for reaction at a reaction temperature of 250-400° C. under a reaction pressure of 1-5 MPa to obtain a pyridine base product.

8. The method for preparing a pyridine base from a syngas according to claim 7, wherein the ammonia donor is selected from one or more of ammonia gas, liquid ammonia and ammonia water, and the pyridine base product comprises one or more of pyridine, 2-methylpyridine, 3-methylpyridine and 4-methylpyridine.

9. The method for preparing a pyridine base from a syngas according to claim 7, wherein the catalyst is subjected to reduction treatment with hydrogen before use, and the reduction treatment is carried out by filling a constant-temperature section of the fixed bed reactor with the catalyst at a hydrogen space velocity of 500-1200 $h^{-1}$ and a reduction temperature of 250-450° C. for a reaction time of 1-5 h.

10. A catalyst for preparing a pyridine base from a syngas, comprising a carrier, an active component, a first auxiliary agent and a second auxiliary agent, wherein the carrier is a molecular sieve, the active component is Rh, the first auxiliary agent is one or more of Mn, Fe, Na and La, and the second auxiliary agent is one or more of Zn, Co, Cr, Bi and Cu, and wherein the active component Rh is 1-3% of the mass of the carrier, the first auxiliary agent is 1.5-5% of the mass of the carrier, and the second auxiliary agent is 5-11% of the mass of the carrier.

* * * * *